United States Patent [19]

Duer

[11] Patent Number: 4,771,785
[45] Date of Patent: Sep. 20, 1988

[54] MAGNETIC RESONANCE IMAGING APPARATUS AND THREE-AXIS PATIENT POSITIONING ASSEMBLY FOR USE THEREWITH

[75] Inventor: Harry R. Duer, Boulder Creek, Calif.

[73] Assignee: Resonex, Inc., Sunnyvale, Calif.

[21] Appl. No.: 890,602

[22] Filed: Jul. 25, 1986

[51] Int. Cl.$^4$ ............................................. A47B 9/16
[52] U.S. Cl. ................................. 128/653; 324/318; 269/322
[58] Field of Search ............... 250/491.1; 324/309, 324/318; 128/653; 378/20, 95, 96, 177, 178, 179, 180, 209; 269/322, 323

[56] References Cited

U.S. PATENT DOCUMENTS

| | | | |
|---|---|---|---|
| 3,965,573 | 6/1976 | Mims | 269/322 |
| 4,034,224 | 7/1977 | Heavens et al. | 269/323 |
| 4,246,802 | 1/1981 | Rasmussen et al. | 74/25 |
| 4,475,072 | 10/1984 | Schwehr et al. | 378/209 |
| 4,567,894 | 2/1986 | Bergman | 128/653 |

FOREIGN PATENT DOCUMENTS

| | | | |
|---|---|---|---|
| 0135161 | 3/1985 | European Pat. Off. | 378/209 |
| 3233363 | 3/1984 | Fed. Rep. of Germany | 269/322 |
| 1159891 | 7/1958 | France | 378/209 |
| 1494017 | 9/1967 | France | 378/209 |
| 0894500 | 4/1962 | United Kingdom | 378/209 |

Primary Examiner—Stewart J. Levy
Assistant Examiner—Lawrence G. Fess
Attorney, Agent, or Firm—Flehr, Hohbach, Test, Albritton & Herbert

[57] ABSTRACT

Magnetic resonance imaging apparatus having a structure with an opening adapted to receive an object to be imaged. An object platform is provided which is sized so that it can be moved into the opening in the magnet structure. Structure is provided for supporting the platform and for moving the platform along x, y and z axes.

13 Claims, 11 Drawing Sheets

FIG.—1

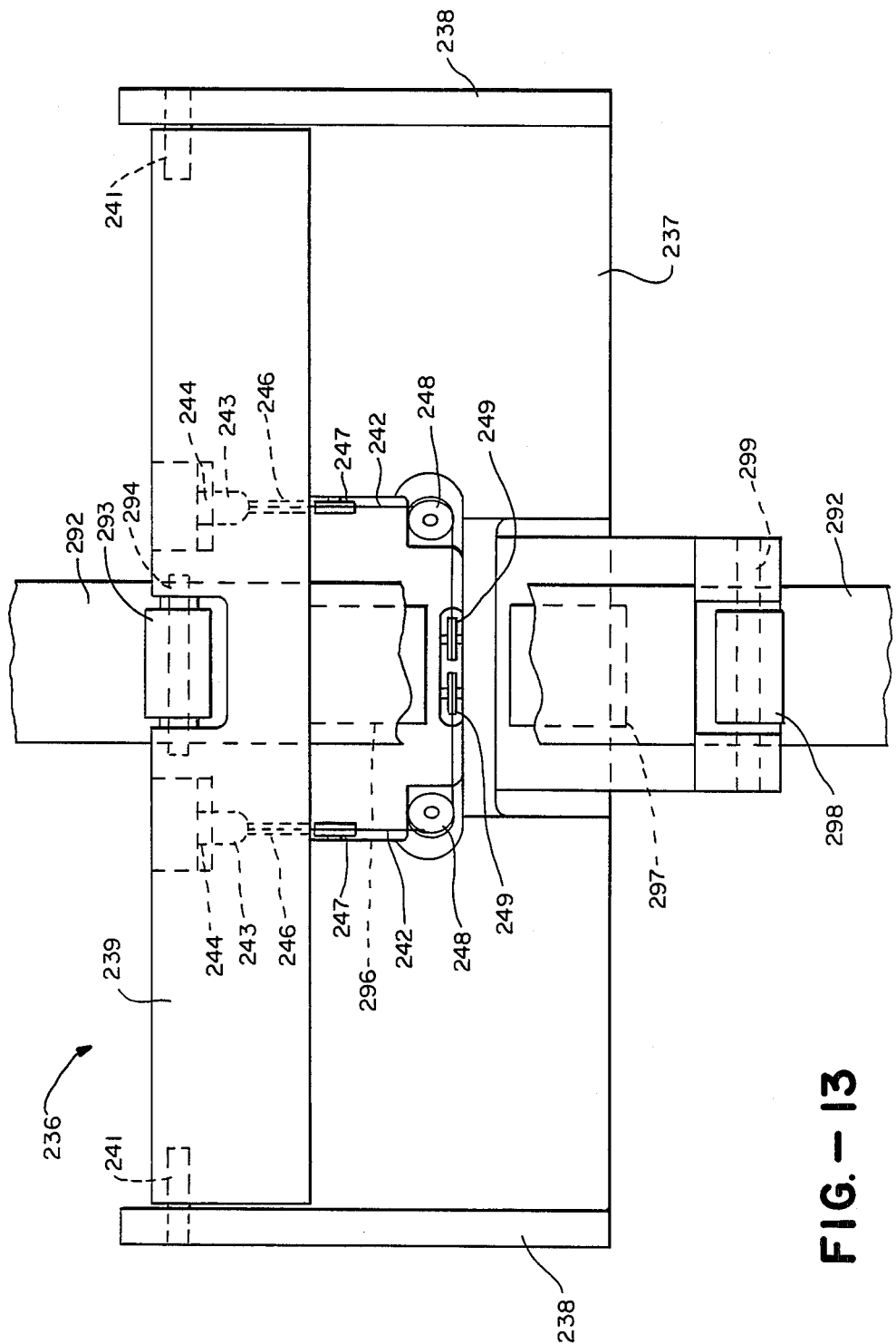

MAGNETIC RESONANCE IMAGING APPARATUS AND THREE-AXIS PATIENT POSITIONING ASSEMBLY FOR USE THEREWITH

This application relates to magnetic resonance imaging apparatus and more particularly to such a magnetic resonance imaging apparatus and a three-axis patient positioning assembly for use therewith.

Magnetic resonance imaging apparatus has heretofore been provided. Such apparatus has also been provided with a patient handling couch which is movable vertically and in and out of the magnet. It has been found that there is a need for a patient couch for use with magnetic resonance imaging apparatus which has additional types of movement available to make it possible to accommodate gurneys of different heights and to facilitate positioning of the patient within the magnet. There is therefore a need for a new and improved magnetic resonance imaging apparatus and more particularly to such an apparatus which has a three-axis patient positioning assembly for use therewith.

In general, it is an object of the present invention to provide a magnetic resonance imaging apparatus and a three-axis patient positioning assembly for use therewith.

Another object of the invention is to provide an apparatus of the above character in which a patient can be moved along x, y and z axes.

Another object of the invention is to provide an apparatus of the above character in which the patient opening in the magnet is at a relatively low elevation.

Another object of the invention is to provide an apparatus of the above character which can readily accommodate different gurney heights for moving the patient from a gurney onto the patient positioning assembly.

Another object of the invention is to provide apparatus of the above character which has a relatively small imaging volume and in which it is possible to shift the patient transversely of the imaging volume, as well as longitudinally of the imaging volume.

Another object of the invention is to provide an apparatus of the above character which eliminates the need for large imaging volumes.

Another object of the invention is to provide an apparatus of the above character which can be readily manufactured.

Another object of the invention is to provide an apparatus of the above character in which three directions of movement can be readily achieved.

Another object of the invention is to provide an apparatus of the above character in which alignment is maintained during the movement along the respective axes.

Another object of the invention is to provide an apparatus of the above character in which limits are provided for the different axes of movement.

Another object of the invention is to provide an apparatus of the above character which is quiet in operation.

Another object of the invention is to provide an apparatus of the above character which is very precise in its operation and has a home position for each axis from which the operation starts.

Another object of the invention is to provide an apparatus of the above character in which the patient couch can be readily removed from the apparatus in the event of an emergency..

Another object of the invention is to provide an apparatus of the above character which includes a quick release mechanism permitting removal of the patient and the patient couch in the event of a power failure or other emergency.

Another object of the invention is to provide an apparatus of the above character in which a drive slot provided for the patient couch is covered during movement of the patient couch.

Another object of the invention is to provide an apparatus of the above character in which various safety features are provided.

Additional objects and features of the invention will appear from the following description in which the preferred embodiment is set forth in conjunction with the accompanying drawings.

FIG. 13 is a cross sectional view showing the details of the quick release mechanism.

In general, the magnetic resonance imaging apparatus of the present invention is comprised of a magnet structure having an opening therein adapted to receive the object to be imaged. An object platform of the size that can be moved into the opening of the magnet structure is provided. Means is provided for supporting the object platform and for moving the same along the x, y and z axes. A manually operated quick release mechanism is provided for separating the object platform from the means for supporting the object platform and for moving the same along the y axis in the event of an emergency.

Figure 1:
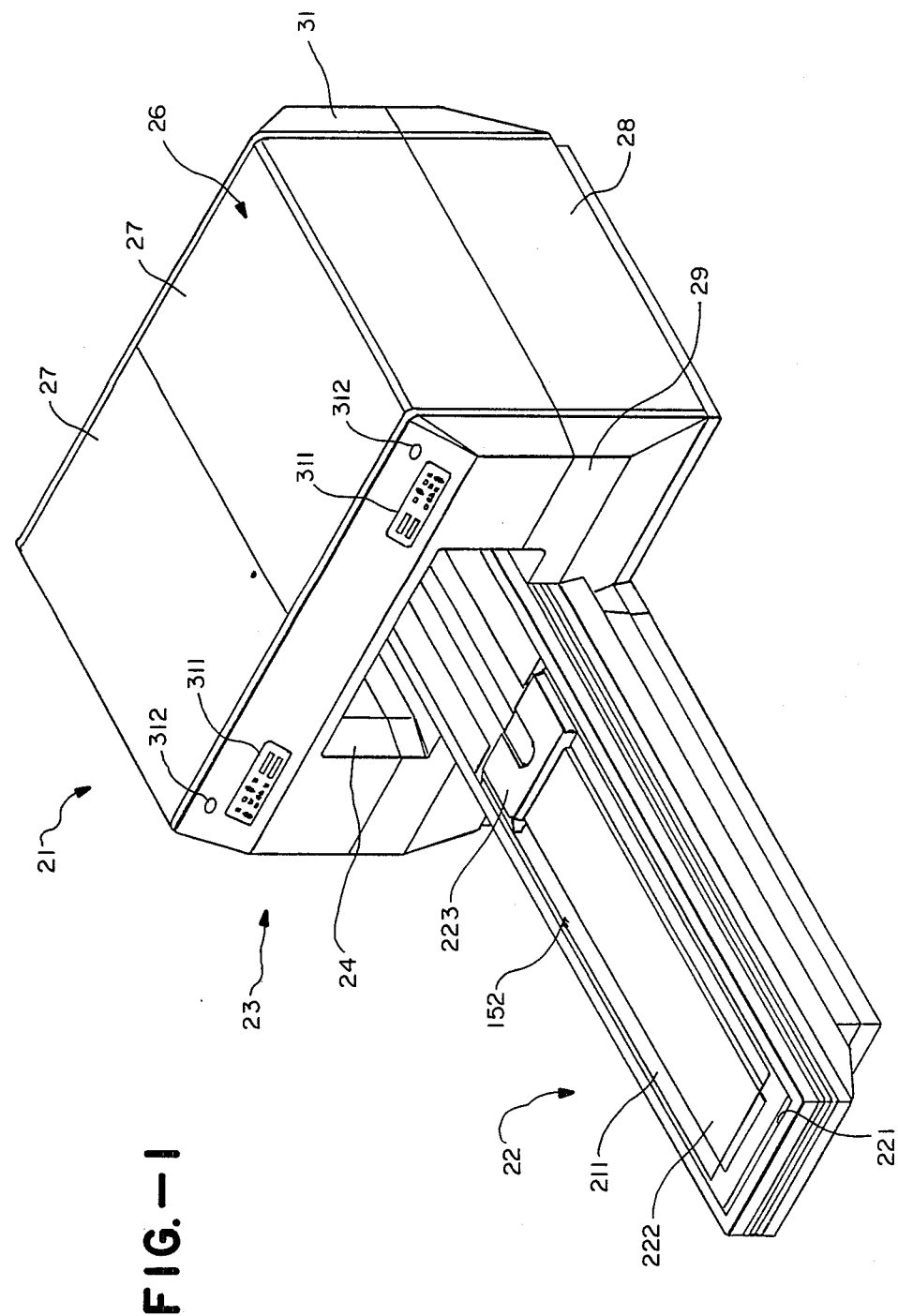
FIG. 1 is an isometric view of a magnetic resonance imaging apparatus and three-axis patient positioning assembly for use therewith incorporating the present invention.

More in particular, the magnetic resonance imaging apparatus 21 shown in FIG. 1 includes a three-axis patient positioning assembly 22 for use therewith. The magnetic resonance imaging apparatus includes a picture frame magnet assembly 23 of the type described in co-pending application Ser. No. 768,872, filed Aug. 23, 1985. As disclosed therein, it provides a rectangular central opening 24 which extends from the front to the rear of the magnet assembly as shown in FIG. 1 and as also disclosed in design patent application, Ser. No. 890,660, filed July 25, 1986. The picture frame magnet assembly 23 is housed within an enclosure or housing 26. The appearance of this enclosure 26 is more fully depicted in the design patent application Ser. No. 890,660, filed July 25, 1986. The enclosure is provided with two gull-wing access doors 27, spaced apart parallel side walls 28 and front walls 29 and 31. The opening 24 provided within the enclosure or housing 26 in one embodiment of the present invention had a size such that the height was approximately 18 inches, the width was approximately 18 inches and the length was approximately 72 inches with the lower extremity of the opening 24 being positioned approximately 24 inches above the ground or floor level for the magnetic resonance imaging apparatus 21.

Figure 2:
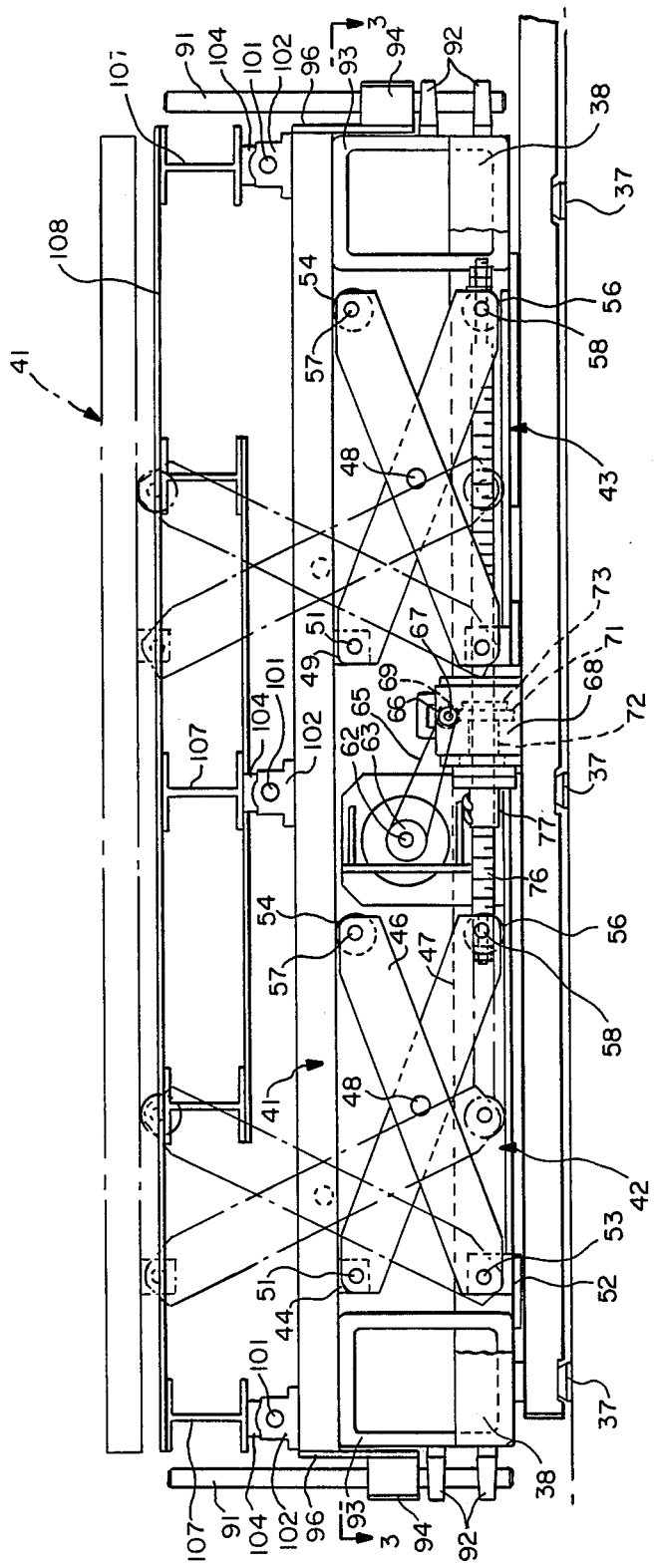
FIG. 2 is a cross sectional view of the three axis patient positioning apparatus shown in FIG. 1 and more, in particular, showing the z-axis mechanism.
Figure 3:
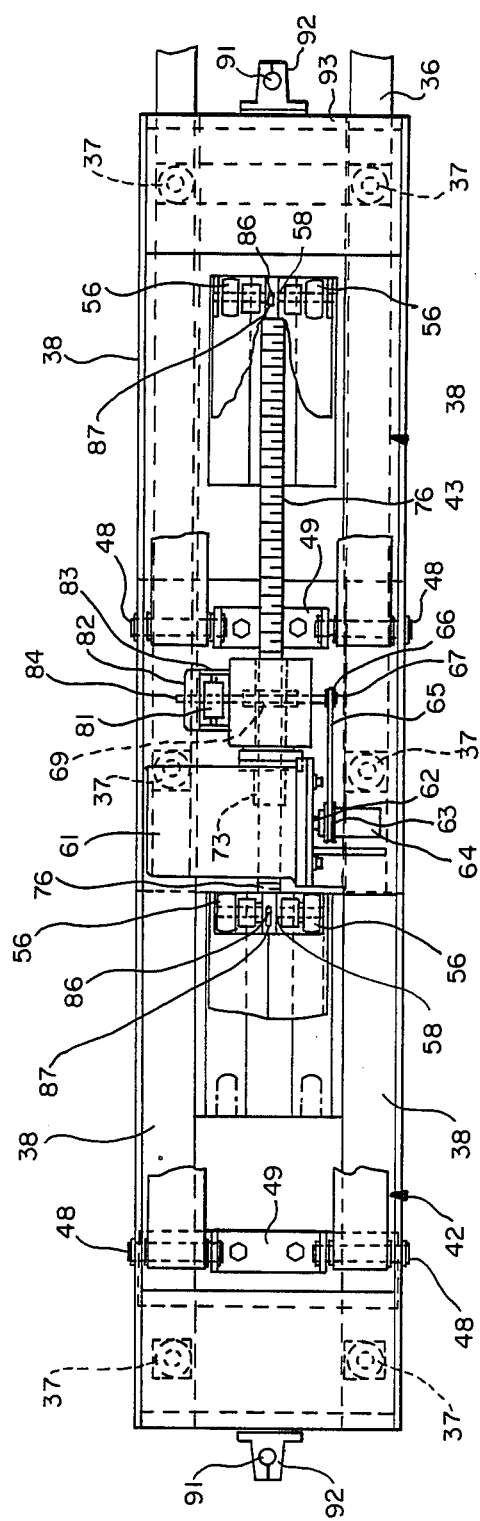
FIG. 3 is a cross sectional view taken along the line 3—3 of FIG. 2.
Figure 4:
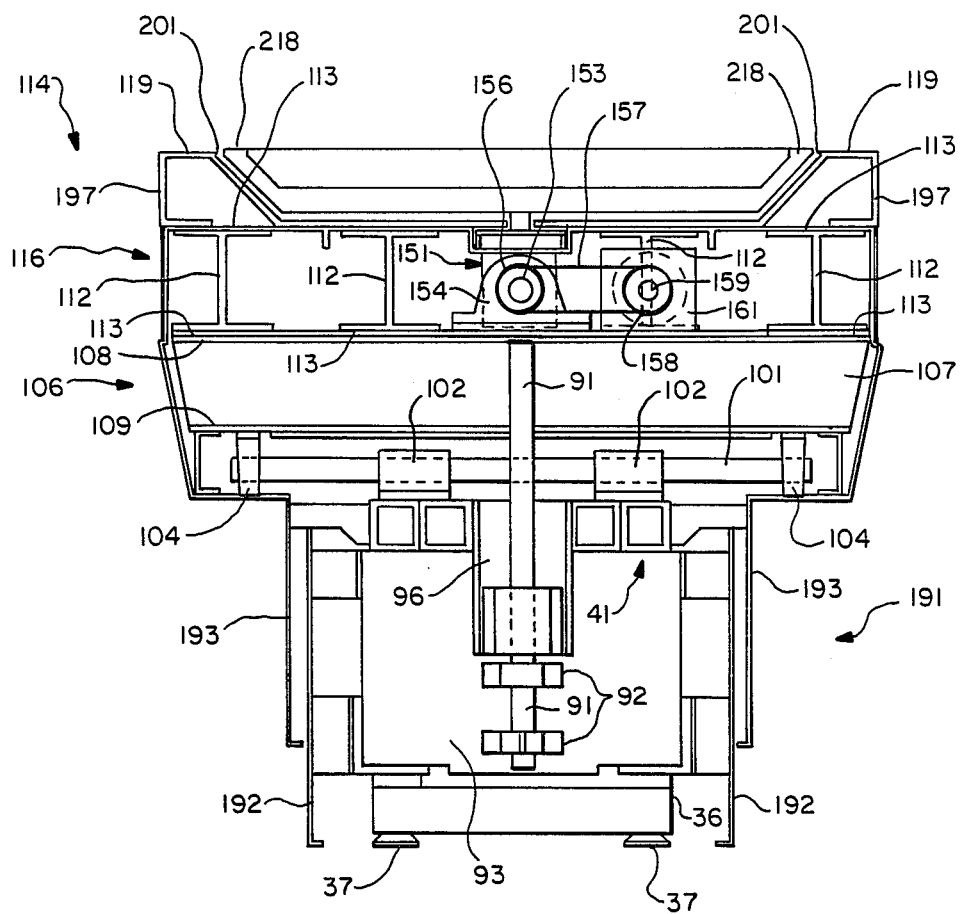
FIG. 4 is an end elevational view showing in particular the y-drive mechanism, the guides for the z-drive mechanism as well as the guides for the x-drive mechanism.
Figure 5:
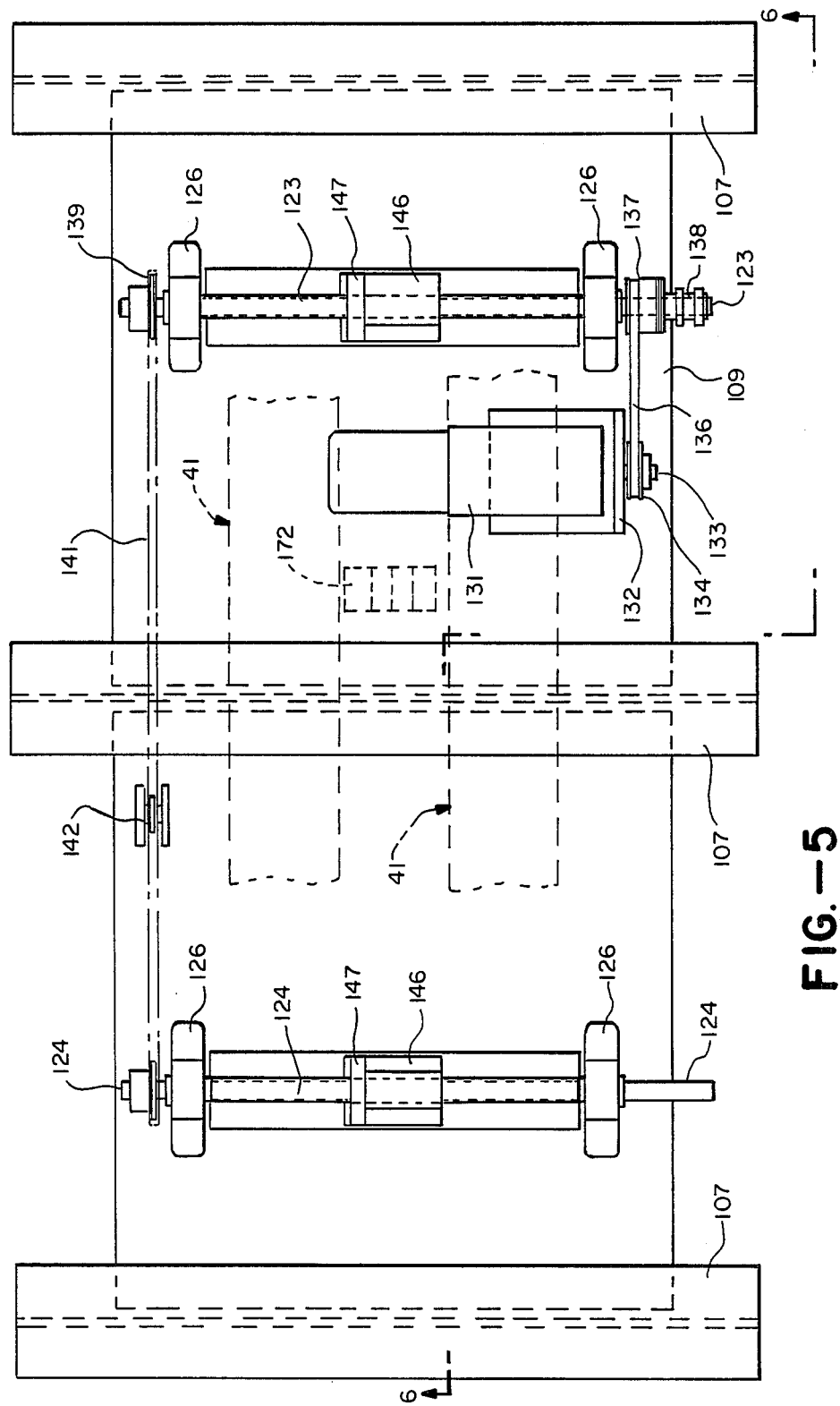
FIG. 5 is a plan view showing the x-drive mechanism.

As can be seen from FIG. 1, the three-axis patient positioning assembly 23 is disposed in front of the front wall 29 of the housing 26 and is in alignment with the patient opening 24 in the magnet structure and extends forwardly therefrom. The three-axis patient assembly consists of a rectangular frame or base 36 which is secured to the frame (not shown) of the magnetic resonance imaging apparatus. The frame 36 is formed of a suitable non-magnetic material such as rectangular aluminum tubing having a dimension of two inches by two inches in cross section. Leveling feet 37 are mounted on the base 36 and are spaced apart longitudinally and transversely of the base 36. A lower Z-frame 38 is mounted on the base 36 in a fixed position. The freame 38 is formed of aluminum angle 3″ ×3″× ⅜″ thick. This lower Z-frame 38 forms a part of and supports the Z-lift mechanism hereinafter described, as shown in FIGS. 2 and 3. The Z-left mechanism also consists of an additional upper Z-frame 51 which lies generally in a plane parallel to the plane of the frame or base 36. The frame 41 is formed of a suitable material such as rectangular aluminum tubing having a dimension of 2 inches by 2 inches. Two pieces of the tubing are welded together for each side of the frame 41 as shown particularly in FIG. 4.

Means is provided for raising and lowering the upper Z-frame 41 with respect to the lower Z-frame 38 along the Z axis or in a vertical direction and consists of a plurality of scissor assemblies 42 and 43. Two of the scissor assemblies 42 are provided on opposite sides of the frames 38 and 41 and similarly two of the other scissor assemblies 43 are provided on opposite sides of the frames 38 and 41. Each of the scissor assemblies 42 and 43 consists of an outer beam 46 and an inner beam 47 which are pivotally interconnected by a wrist pin 48 intermediate the ends of the same. One end of each of the inner beams 47 is secured to a bracket 49 by a wrist pin 51. The bracket 49 is secured to the upper frame 41. Similarly, one end of the outer beam 46 is secured to a bracket 52 by a wrist pin 53. The bracket 52 is secured to the upper side of the lower Z-frame 38 as shown in FIG. 2. The other ends or free ends of the inner and outer beams 46 and 47 have rollers 54 and 56 rotatably mounted thereon. The rollers 54 and 56 are formed of a suitable material such as polyurethane to minimize friction and to reduce any galling. The rollers 54 are adapted to engage the lower side of the framework 41 and are rotatably secured to the ends of the outer beams 46 by suitable means such as wrist pins 57. The rollers 56 are adapted to engage the upper side of the lower Z-frame 38 and are rotatably mounted upon axles 58 which extend between the ends of the inner beams 47.

Means is provided for operating the outer and inner scissor assemblies 42 and 43 to cause relative movement with respect to the frames 38 and 41 in a z or vertical direction and consists of a motor 61 mounted upon the lower z-frame 38 of a suitable type as, for example, a 60 cycle 110 volt ½ horsepower motor operating at 1750 rpm. As shown in FIGS. 2 and 3, the motor 61 is mounted between the outer and inner scissor assemblies 42 and 43. The motor 61 is provided with an output shaft 62 which drives a pulley 63 through a friction clutch assembly 64. The pulley 63 drives a belt 65. The belt 65 drives a pulley 66 mounted on the input shaft 67 of a gear box assembly 68 which can be identified as the z-axis gear box assembly. The gear box assembly 68 comprises a right angle worm drive which includes a worm 69 which is rotated by the shaft 67. The worm 69 drives a worm gear or ring gear 71 which rotates in a direction at right angles to the direction of rotation of the worm 69 and the shaft 67. The ring gear 71 is secured to a bearing tube 72 by a bearing nut 73. The bearing tube 72 has a suitable diameter such as two inches. A ball screw shaft 76 extends through the bearing tube 72 and is threadedly mounted in a ball screw nut extends through the bearing tube and is threadedly mounted in a ball screw nut 77. The ball screw nut 77 is secured to the bearing tube 72 so that it rotates with the bearing tube. A brake and clutch assembly 81 is secured to the worm shaft 67 to provide braking when required as for example when power is terminated. The brake assembly 81 is of a conventional type which uses spring means (not shown) for causing engagement of the brake assembly and solenoid operated means (not shown) for disengaging the brake assembly. Manual operated means in the form of a release lever 82 pivotally mounted at 83 for overcoming the spring means to disengage the brake assembly 81. A square end 84 is provided on the end of the worm gear shaft 67 which can be engaged by a crank whereby the worm 69 can be rotated to cause raising or lowering of the frame 41 relative to the frame 36 in the event of a power failure.

Suitable means is provided for securing the opposite ends of the ball screw shaft 76 to the axles 58 and consists of anti-rotation pins 86 secured to the shafts 56 and extending through slots 87 provided in the ball screw shaft 76. The pin and slot connections make possible overrun at the end of travel which serves to prevent jamming of the apparatus.

Means is provided for ensuring that the upper frame 41 will move in a vertical direction as it is being raised and lowered with respect to the frame 36 and consists of a vertical shaft 91 mounted at each end of the frame 38. The vertical shafts 91 are carried by a pair of spaced apart shaft mounts 92 secured to one side of box shaped structures 93 mounted on opposite ends of the frame 38. The shafts 91 travel through linear bearings 94 which are secured to plates 96 extending downwardly and mounted on opposite ends of the upper frame 41. It can be seen from this construction that the two spaced apart parallel vertical shafts 91 guide the frame 41 in a vertical direction as it is raised and lowered. These guides 91 make it possible to provide scissor assemblies 42 and 43 of lesser precision.

As hereinafter explained when it is desired to raise and lower the frame 41, the motor 61 is energized to cause operation of the gear box 68. At the same time, the spring loaded brake assembly 81 is energized to permit rotation of the worm 69. Rotation of the worm 69 causes rotation of the worm gear 71 and the bearing tube 72 and the bearing nut 73 carried thereby. Since the ball screw shaft 76 cannot rotate, as the ball screw nut 77 is rotated, the ball screw shaft 76 is advanced in one direction or the other depending on the direction of rotation of the ball screw nut 77.

Let it be assumed that the rotation of the ball screw nut 77 is in such a direction so as to cause movement of the ball screw shaft from the right to the left as viewed in FIG. 1. As this occurs, the right-hand end of the inner scissor assembly 43 and similarly, the right-hand end of the outer scissor assembly 42 will be moved to the left. As this movement to the left occurs, the rollers 56 will travel on the frame 38 to cause raising of the upper frame 41. This raising continues until the extreme uppermost position for the upper frame 41 has been attained as, for example, as shown in the broken lines in FIG. 2. With this arrangement it can be seen that the shaft 58 on the inner scissor assembly 43 is pulled and the shaft 58 of the outer scissor assembly 42 is pushed. Thus it can be seen that the pair of beams of both scissor mechanisms are moved simultaneously to cause the frame 41 to be moved upwardly in a parallel relationship to the frame 36. The upper extreme position for the frame 41 is shown in FIG. 2 in broken lines. The lowermost position for the frame 41 is shown in solid lines in FIG. 2.

As soon as the desired elevation has been reached for the frame 41, the motor 61 is de-energized and the solenoid operated clutch brake assembly 81 is also de-energized so that it is spring loaded into a braking position to hold the frame 41 at the desired elevation. If the break assembly 81 were not provided, the weight of the frame 41 and the structure carried thereon as hereinafter described would be sufficient to cause rotation of the ball screw nut to permit the frame 41 to descent to its lowermost position. The lowermost position as shown in FIG. 2 is determined by the box shaped end block structures 93 hereinbefore described.

When it is desired to lower the frame 41, the motor 61 is operated in a reverse direction to cause movement of the ball screw shaft 76 to the right as viewed in FIGS. 2 and 3 which causes lowering of the frame 41. This lowering can continue until the stops provided by the box-shaped end blocks 93 are engaged by the lower surfaces of the frame 41.

From the foregoing, it can be seen that the three-axis patient positioning assembly has been described to the extent that the z-motion or motion in a vertical direction has been provided. The mechanism for achieving motions along the two other axis, namely, the x and y axis may now be described.

The x-axis movement is provided by three spaced parallel shafts 101, which are carried by six linear bearings 102 that are mounted on spaced apart locations on opposite sides of the frame 41. A pair of shaft mounts 104 are provided on each of the shafts 101 and are fixed to the ends of the shafts 101 (see FIG. 4) outside of the linear bearings 102. Thus there are provided six such shaft mounts 104. The shaft mounts 104 are secured to an x frame structure 106. The x frame structure 106 is comprised of five I beams, 107 formed of a suitable material such as fiberglass having approximate dimensions 4 inches by 4 inches in cross section. The x frame structure 106 is also comprised of two spaced apart lower metal sheet 109 formed of a suitable material such as aluminum and which are mounted on the lower surfaces of the I beams 107 and secured thereto to form a composite beam structure for the x frame structure 106.

As can be seen particularly from FIG. 2, the shaft mounts 104 are secured to the x frame structure 106 in regions immediately below the I beams 107. The five spaced parallel I beams extend in an x direction and with the metal plates 109 form the x beam structure 106.

The y frame structure 116 also includes four spaced apart and parallel I beams 112 of a suitable length as, for example, 111 inches which extend in the y direction. The y-frame structure is also comprised of four metal sheets 113 formed of a suitable material such as aluminum and which are mounted on the top and bottom of the y-beams 112, in pairs, to form two composite beams forming the y-structure 116, shown in FIG. 4. The composite y-beams overlie and are secured to the five x-beams to form a combinatio x-y structure 114 (See FIG. 4).

Drive means is provided for driving the x-y combination structure 114 in a x direction and consists of a pair of spaced parallel I beams 121 which are mounted upon the frame 41. The I beams 121 are formed of a suitable material such as fiberglass and have a cross-sectional dimension of approximately 2 inches by 2 inches. Metal L-shaped brackets 122 overlie the top of are secured to the I beams 121.

First and second spaced parallel shafts 123 and 124 overlie the I beams 121. Each of the shafts 123 are mounted in a pair of spaced apart pillow block bearings 126 mounted on the plate 109 immediately over the I beams 121. Means is provided for driving the shaft 123 and consists of a DC servo motor drive 131 mounted upon a mounting bracket 132 that is secured to the plate 109. The DC servo motor drive 131 is provided with an output shaft 133 which has a pulley 134 affixed thereto. The pulley 134 drives a drive belt 136 which drives another pulley 137 that is mounted on the shaft 123. A mechanical clutch mechanism 138 is provided on the outboard end of the shaft 123. A pulley 139 is mounted on the other end of the shaft 123 and drives a slave belt 141. The slave belt 141 passes over an idler 142 and drives a pulley 143 which is secured to one end of the shaft 124 for driving the shaft 124.

The shafts 123 and 124 are ball screw shafts and have a ball screw nut 146 which is mounted thereon between the bearings 126. The ball screw nut 146 is held in position so that it cannot rotate by a bracket 147 which is secured directly to the I beams 121 and the metal plates 122. Since the ball screw nut 146 is held so that it cannot rotate, it can be seen that as the shafts 123 and 124 are rotated the ball screw nuts 146 will be translated in an x direction axially of the shafts 123 and 124 within limits of movement as hereinafter described between the pillow block bearings 126. It can be seen that a double point drive has been provided by the x drive for the x-y beam structure 114 to prevent the x beam structure from skewing off the center line. Since the shaft 124 is slaved to the shaft 123, such skewing of the x-y structure 114 is eliminated so as to prevent misalignment. From the foregoing it can be seen that ball screws have been utilized for the z direction and x direction drives.

Means has been provided for driving the patient sled assembly 152 in the y direction which comprised of an axial gear or linear friction actuator of the type described in U.S. Pat. No. 4,246,802 and of the type manufactured and sold by International Design Logistics, Inc., of Santa Barbara, Calif. The linear actuator 151 is comprised of upper and lower parts 151a and 151b in which the upper part 151a is secured to the bottom side of a patient sled assembly 152. The part 151b is secured to the part 150a so that both of the parts 151a and 151b engage a long shaft 153 which extends the length of the y beam structure 116 disposed between the I beams 112 equidistant between the sides of the y frame in y-beam structure 116. The opposite ends of the shaft 153 are rotatably mounted in a pair of pillow block bearings 154 provided on each end and which are supported upon the lower plates 113. A pulley 156 is mounted on one end of the shaft 153 and is driven by a belt 157. The belt 157 is driven by a pulley 158 mounted on the output shaft 159 of a DC servo motor drive 161 which is also mounted upon the lower plate 113. When the DC servo motor drive 161 is operated, the shaft 153 is rotated which causes a load to be applied to the linear actuator 151. This causes the lower housing 151b to be drawn up to the upper housing 151 to frictionally engage the shaft 153 and to cause translational movement of the patient sled assembly 152 in a y direction or in a direction parallel to the axis of the shaft 153. No cluch is required in the y drive because the friction drive linear actuator 151 provides the necessary clutching action when required. It should be appreciated that if desired a ball screw drive and clutch assembly of the type hereinbefore described for the z and x drives can be substituted for the linear friction drive.

Figure 6:
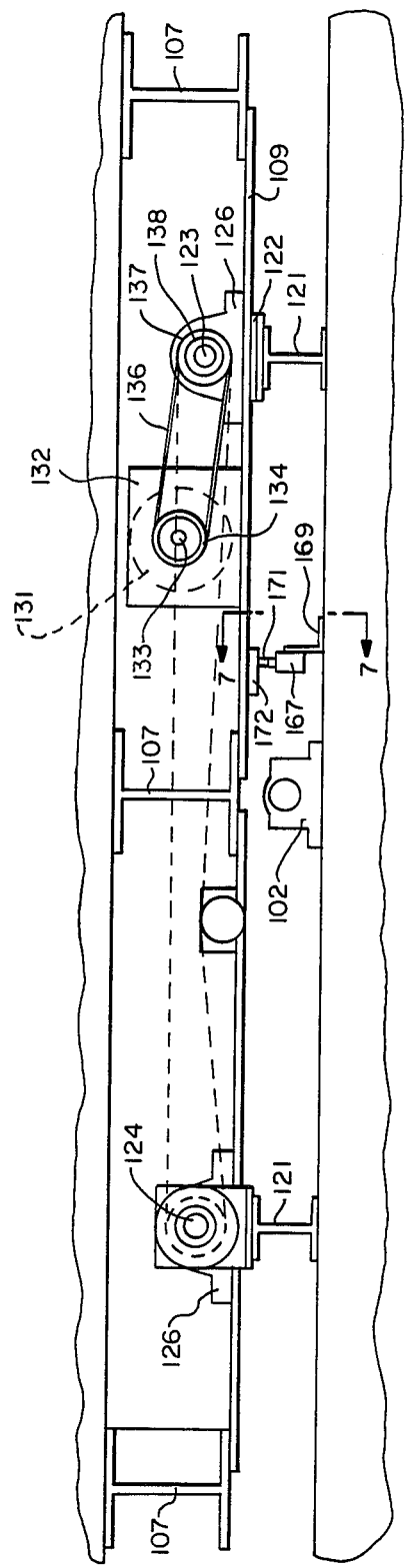
FIG. 6 is a partial cross sectional view showing additional portions of the x-drive mechanism.
Figure 7:
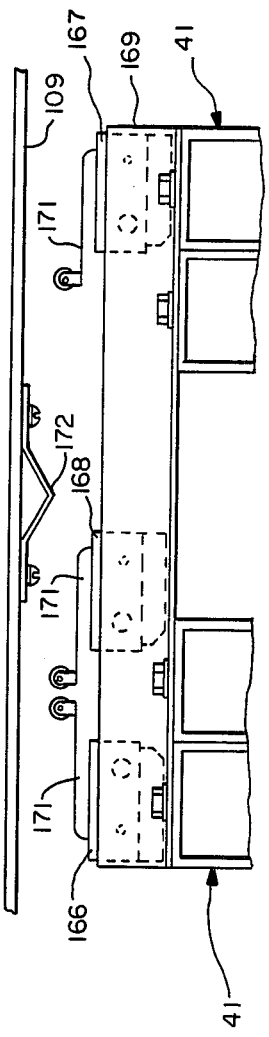
FIG. 7 is a cross sectional view taken along the lines 7—7 of FIG. 6.

The DC servo motor drive 161 for the y direction of movement and the DC servo motor drive 131 for the x direction of movement can be supplied with power in a suitable manner. A suitable DC servo controller card is one supplied by Delta Tau Systems, Inc. of 21115 Osborne Street, Canoga Park, Calif. Means is provided in conjunction with these control cards for limiting the movement of the patient couch assembly 152 in the x and y directions. Three of such limit switches are provided for the x direction and consists of two limit switches 166 and 167 for giving the extreme positions for the x movement and an additional limit switch 168 which provides a "home" position for the patient couch assembly in the x direction. These x direction limit switches are shown in FIGS. 6 and 7. All three of the limit switches 166, 167 and 168 are mounted upon a bracket 169 which is secured to the frame 41. Each of the limit switches 166, 167 and 168 is provided with an operating arm 171 which is adapted to be engaged by a V-shaped detent 172 carried by the plate 109 of the x beam structure 111. The two other limit switches 166 and 167 interrupt the power to the DC servo motor drive 131 to stop the movement of the x beam structure 111 within the mechanical limits of the three-axis patient positioning assembly 22. The third switch 168 provides a home position in the x axis for the patient couch assembly 152 and provides an initial point of travel for the software controlled servo system driving the DC servo motor drive 131.

Figure 12:
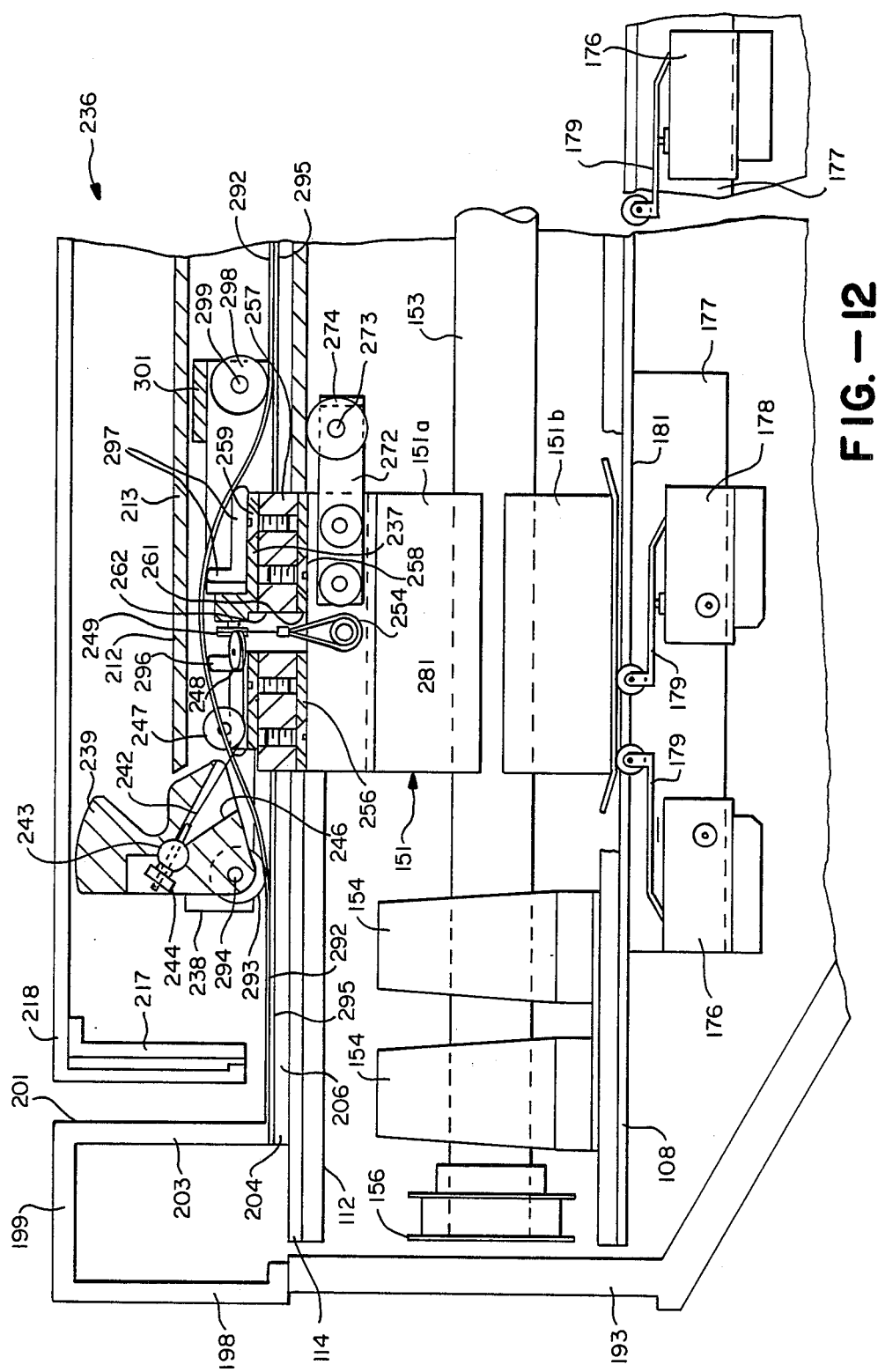
FIG. 12 is a cross sectional view showing the y axis drive mechanism and the quick release mechanism used with the patient couch assembly and the band guide utilized in connection therewith.

A similar limit switch arrangement has been provided for the y direction of movement and includes a pair of limit switches 176 disposed at opposite ends of the y beam structure 116 and secured thereto by suitable means such as brackets 177. An additional limit switch 178 is provided between the limit switches 176 and serves as the home limit switch. It is also secured to one of the brackets 177. The limit switches 176 and 178 are provided with operating arms 179 which are adapted to be engaged by a detent 181 carried by the housing portion 151b of the linear actuator 151 (see FIG. 12). The two outer limit switches 176 serve to cut off the power and serve as mechanical limits for movement in the y direction whereas the limit switch 178 provides a home limit switch or a zero position for the software controlled DC motor drive 161.

Figure 8:
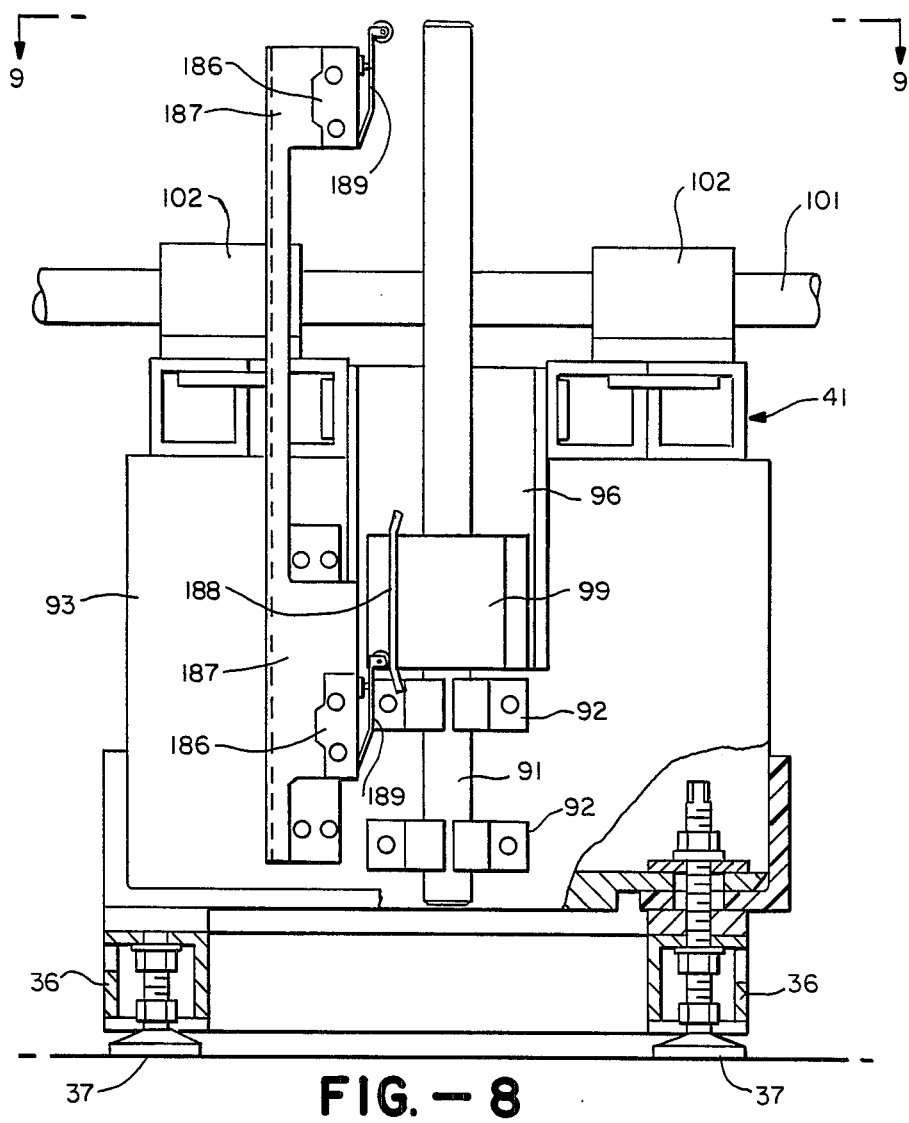
FIG. 8 is an elevational view partially in cross section showing the z-axis limit switches.
Figure 9:
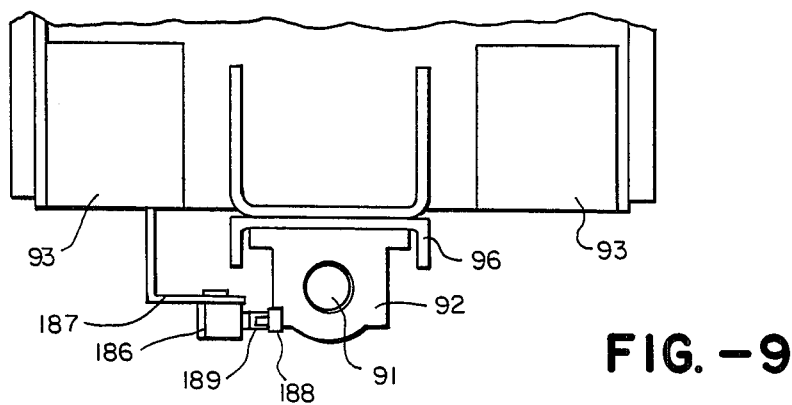
FIG. 9 is a cross sectional view taken along the line 9—9 of FIG. 8.
Figure 10:
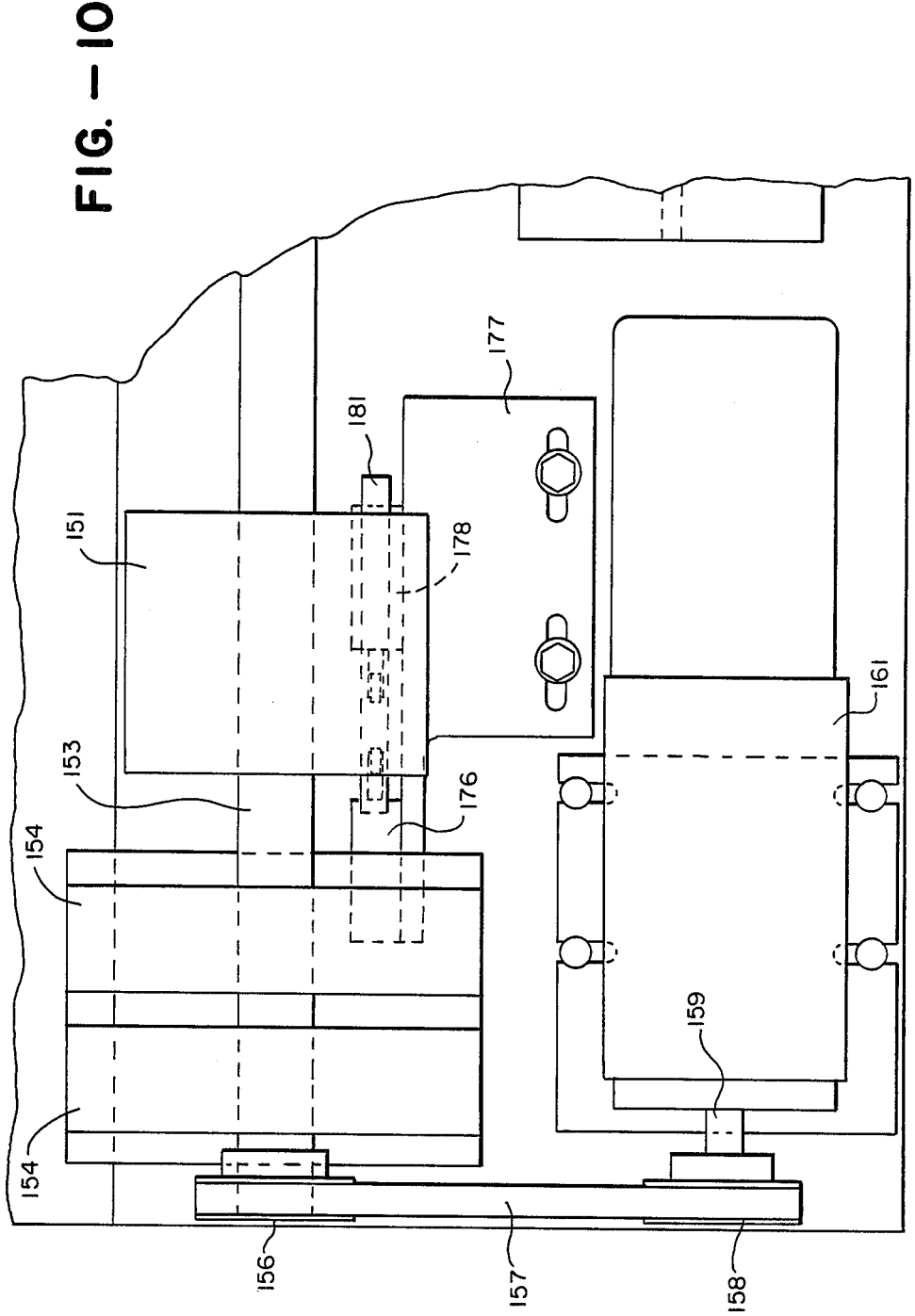
FIG. 10 is a view showing the y-axis drive mechanism.
Figure 11:
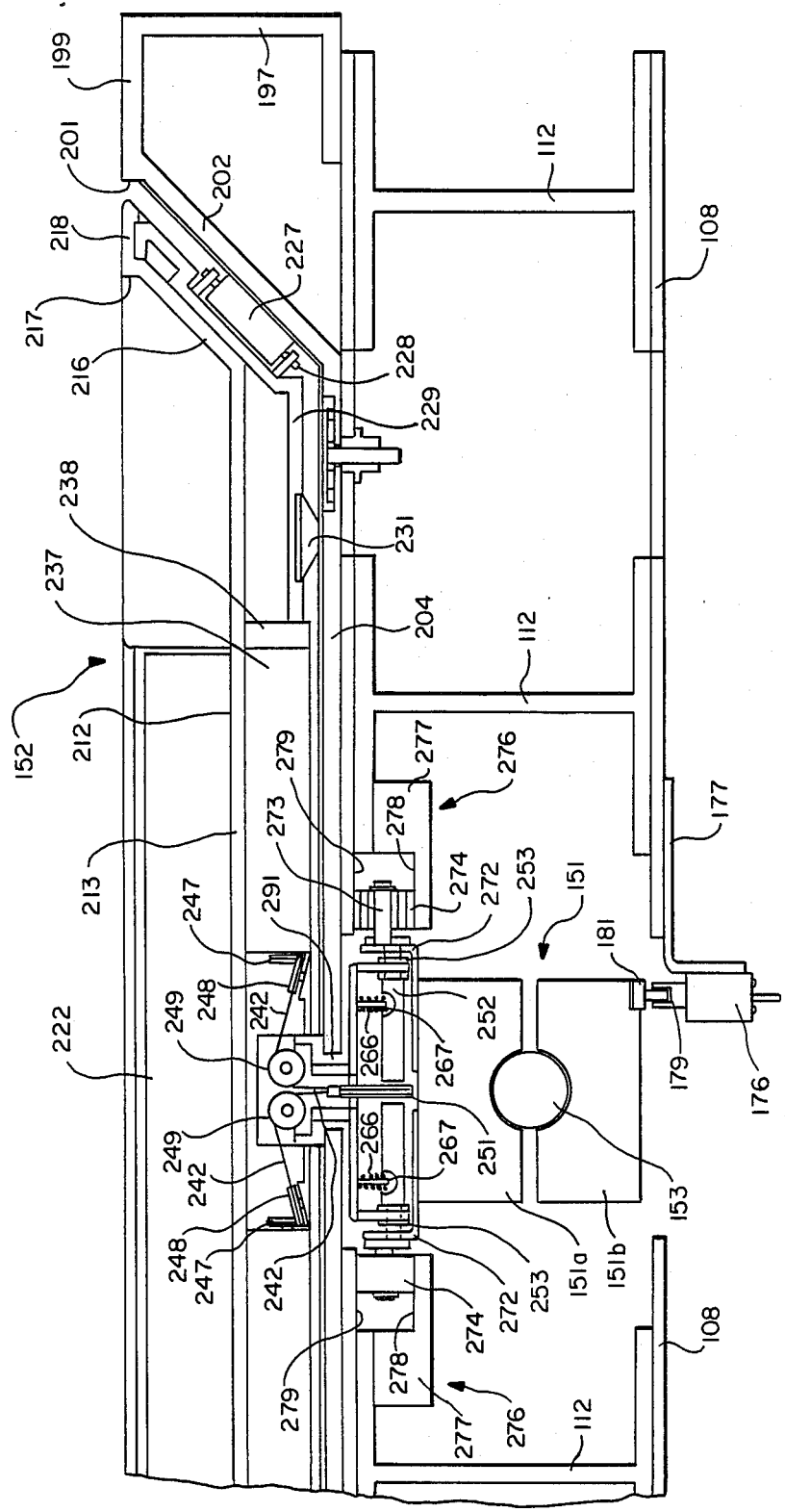
FIG. 11 is a cross sectional view showing in particular the y drive mechanism and the patient couch assembly with a quick release mechanism.

Similar limit switch means is also provided for the z direction of movement and as shown particularly in FIG. 8 consists of a pair of limit switches 186 mounted upon an upper bracket 187 which is mounted upon the box-shaped structure 93. The limit switches 186 are mounted on the extreme limits of travel of the frame 41 in the z vertical direction. The limit switches 186 are provided with operating arms 189 which are adapted to be engaged by detent 188 mounted on a linear guide bearing 99 carried movably on the shaft 91.

An enclosure 191 is provided for the three-axis patient positioning assembly 22 and is comprised of side panels 192 positioned on opposite sides of the frames 41 and 42. Additional side panels 93 are provided which extend upwardly from the side panels 93 and serve to enclose the x-y frame structure 106.

The patient couch assembly 152 includes a rectangular framework 196 formed of a suitable material such as fiberglass which is mounted upon the plates 113 carried by the I beams 112. This framework 196 is provided with spaced parallel vertical side walls 197 and vertical end walls 198. The side and end walls 197 and 198 adjoin a top wall 199 which is provided with a rectangular opening 201 therein.

The top wall 199 of the framework 196 adjoins spaced parallel downwardly inclined side walls 202 and spaced parallel substantially vertical end walls 203. The side walls 202 and the end walls 203 adjoin a substantially horizontal bottom wall 204. The bottom wall 204 is provided with a slot 206 which extends longitudinally along the y axis of the bottom wall for a purpose hereinafter described. Inclined side walls 202 serve as a track also for a purpose hereinafter described.

The patient couch assembly 152 includes the patient couch 211 in the form of a sled. It is also formed of a suitable material such a fiberglass and is provided with a top planar surface 212 provided by a horizontal top wall 213. The wall 213 adjoins upwardly inclined spaced parallel side walls 216 and spaced parallel vertically extending end walls 217. The side walls 216 and the end walls 217 adjoin a horizontal top wall 218. The walls 213, 216, 217 and 218 cooperate to provide a rectangular recess 221 which is open through the top side in which a cushion 222 and a headrest 223 of a suitable material such as foam rubber can be placed.

Means is provided for facilitating movement of the patient couch or sled 211 along the y axis within the framework 196 and consists of a layer 226 of a suitable material such as Formica which is disposed on the inclined side walls 202. It is also comprised of rollers 227 carried by brackets 228 mounted upon a member 229 which is secured to the side walls 216. The rollers 227 are formed of a suitable material such as nylon.

Slides 231 of a generally truncated triangular shape are carried by the members 229 and are also formed of a suitable material such as fiberglass and adapted to ride upon the bottom wall 202 of the framework 196.

Manual quick release coupling means 236 is provided for coupling the patient couch or sled 152 to the y drive means and more in particular to the linear actuator 151. Such means is comprised of a mounting plate 237 which is rectangular in configuration and is formed of a suitable material such as aluminum. The mounting plate 237 is provided with a pair of end plates 238 which are secured thereto and extend upwardly therefrom. A handle 239 is pivotally mounted on pins 241 carried by the upper extremities of the end plates 238. A length of cable 242 of a suitable material such as stainless steel is secured to the handle 239. The cable 242 has its opposite ends connected to spaced apart locations on the handle 239 by a turn buckle 243 which is seated in the handle and a self-locking nut 244 which engages the turnbuckle. The cable 242 passes through slots 246 provided in the handle 239 and passes over pairs of pulleys 247, 248 and 249 carried by the mounting plate 237 and thence over a thimble 251 carried by a latch pin 252. A pair of rollers 253 of a suitable material such as nylon are mounted on opposite ends of the latch pin 252. The rollers 253 are disposed in elongate slots 254 provided in a U-shaped bracket 256. The U-shaped bracket 256 is secured to a block 257 of a suitable material such as nylon by screws 258. The block 257 is secured to the mounting plate 237 by suitable means such as screws 259. The U-shaped bracket 256 and the block 257 are provided with holes 261 and 262 through which the cable 242 extends.

The latch pin 252 is spring loaded in a downward direction by a pair of springs 266 mounted on rods 267 which are seated in the latch pin 252 so that the springs 266 continuously and yieldably apply downward forces to the latch pin 252.

Means is carried by the linear actuator 151 which is adapted to be releasably engaged by the latch pin 252 and consists of C-shaped brackets 272 which are secured to the upper extremity of the linear actuator housing 151a. A shaft 273 is mounted on the L-shaped brackets 272 and carry rotatably mounted thereon anti-rotation rollers 274 formed of a suitable material such as Nylon. The rollers 274 travel in two track structures 276, each of which consists of an L-shaped member 277 which is secured to the upper flange of the I beam 112 to provide one surface 278 for the rollers 274 in cooperation with another surface 279 provided by the lower side of the plate 113. The bracket 272 is provided with vertically extending slots 281 open at their top ends in which the rollers 253 carried by the end of the latch pin 252 can be seated.

The anti-rotation rollers 274 serve to prevent the linear actuator from rotating with the shaft 153 as it is rotated. The anti-rotation rollers 274 also serve to support the shaft 153 throughout its length, in other words, to keep the shaft 153 from sagging.

It can be seen that with the quick release coupling mechanism 236 herein provided that in the event of a power failure and the patient is within the magnet structure, the patient can be quickly removed from the patient structure by grabbing the handle 239 which decouples the sled from the y drive by pulling the latch pin 252 upwardly against the force of the springs 266 to clear the slots 281. The patient sled or couch 252 can then be pulled manually out of the magnet with a relatively small amount of effort. Such a manual quick release coupling mechanism is advantageous in the event of a power failure and also in case of a medical emergency with respect to removal of the patient from the magnetic resonance imaging apparatus.

The manually operated quick release coupling mechanism 236 hereinbefore described extends downwardly through a drive slot 291 which extends longitudinally between the upper plates 113 of the y beam structure. In order to improve the appearance of the magnetic resonance imaging apparatus, means is provided for covering this drive slot as the patient sled or couch is advanced into the magnet structure 223. In addition, such means is desired to prevent articles such as sheets and the like from falling through the drive slot and also to keep out the dust. It also serves as a protective measure to keep fingers of the hand and the like from passing through the slot. This means is comprised of a flexible band 292 of a suitable material such as stainless steel. The band 292 is maintained over the drive slot by means of rubber magnet strips 295 bonded to both sides of the drive slot 291. The band 292 travels under a roller 293 of a suitable material such as Nylon that is rotatably mounted in the handle 239 by a pin 294. The band 292 then travels over a pair of spaced apart skids 296 and 297 which are provided as a part of the quick release mechanism and are mounted upon the mounting plate 237. The band 292 then travels under another roller 298 of a suitable material such as Nylon rotatably mounted on a pin 299 mounted in a bracket 301 which forms a part of the quick release mechanism 236. Thus it can be seen that the patient couch or sled 211 can be moved along the y axis longitudinally of the x-y frame structure 114 while permitting use of the quick release coupling mechanism 236 that extends through the drive slot 291. As hereinbefore described means is provided within the quick release coupling mechanism 236 to permit the band to travel over the quick release mechanism and then to lay the same down on both sides of the quick release mechanism so that the drive slot 291 remains substantially covered at all times.

A pair of control panels 311 are provided on the front wall 29 of the enclosure 26 so that operation of the apparatus can be carried out by an operator on opposite sides of the patient couch 22. Emergency power off buttons 312 are also provided adjacent the control panels 311 to shut down the magnet and couch power in case of an emergency.

Operation and use of the magnetic resonance imaging apparatus and the three-axis patient positioning assembly for use therewith may now be briefly described as follows. Let it be assumed that it is desired to place a patient in the patient imaging apparatus. Let it also be assumed that the controls of the magnetic imaging apparatus are in a position so that the x, y and z mechanisms are in their home positions. As soon as the gurney carrying the patient has been brought alongside the three-axis patient positioning apparatus 22, the z axis mechanism can be placed in operation to raise the patient couch 22 to approximately the same level as the gurney. The patient then by himself rolls over onto the couch or is lifted onto the couch. The z-axis mechanism is again operated to lower the couch into a position so that it can enter into the opening 24 provided in the magnet structure. The patient can be then advanced into the magnet structure by operation of the y mechanism. In addition, the patient can be moved in the x direction. Thus it can be seen that it is possible to position the patient precisely within the magnet structure. In addition, it is possible to move the patient within the magnet structure so that a particular organ or organs are in a position in which they can be most efficaciously imaged.

In the event of a power failure or in the event of a medical emergency with respect to the patient, the patient couch can be readily removed from the magnet structure by grasping the handle 239. Grasping the handle 239 causes movement of the latch pin 252 against the force of the springs 266 to release the same from the linear actuator 151 for the y drive permitting the patient couch with the patient thereon to be pulled rapidly out of the magnet structure to take whatever additional procedures are thereafter needed with respect to the patient.

The drive mechanisms which have been provided to give the three axes of movement for the patient positioning assembly have been constructed in such a manner that they are very quiet and precise in their operation. In addition the movements which are provided are quiet and smooth in operation without any jerkiness. Adequate safety has been provided by the use of a limit switches hereinbefore described and the electronic controls associated with the operation of the various drive mechanism.

What is claimed is:

1. In a magnetic resonance imaging apparatus, a structure having an opening and adapted to receive an object to be imaged, an object platform sized so that it can be moved into the opening in the magnet structure, means for supporting said object platform and power actuator means for moving said object platform along a y axis into and out of the opening, said power actuator means including a manually-operated quick release mechanism for separating the object platform from said power actuator means in the event of a power failure whereby the object platform can be rapidly removed from the structure through said opening, said quick release mechanism including a handle adapted to be grasped by the human hand and cooperative manually-operated means secured to the handle and forming a releasable connection between the object platform and the power actuator means.

2. Apparatus as in claim 1 wherein said power actuator means includes a servo controlled direct current motor means.

3. Apparatus as in claim 1 together with power actuator means for moving the object platform along an x axis and including a servo controlled DC motor.

4. In a magnetic resonance imaging apparatus, a structure having an opening adapted to receive an object to be imaged, an object platform sized so that it can be moved into the opening in the magnet structure, means for supporting said object platform, power actuator means for moving said object platform along a y axis into and out of the opening, power actuator means for moving the object platform along a z axis and including a first and second scissor assemblies spaced apart in a horizontal direction, each scissor assembly having a pivot axis and comprising inner and outer members, screw means, nut means rotatably mounted on the screw means, means for rotating the nut means and means for securing the screw means to at least one member of each of the scissor assemblies to cause each of said one member to be moved about the pivot axis for the associated scissor assembly for causing raising and lowering of the object platform.

5. Apparatus as in claim 4 together with vertical guide means for guiding the movement along the z axis.

6. In a three-axis patient positioning assembly for use with a magnetic resonance imaging apparatus of the type having a magnet structure with an opening therein, a base, a frame, at least first and second horizontally spaced apart scissor assemblies supporting said frame on said base for movement of said frame with respect to said base in a vertical or z direction, each of said scissor assemblies including first and second members which are pivotally innerconnected intermediate the ends of the same, means for fixing one end of one of the members of each scissor assembly to the base and one end of the other member to the frame, rollers carried by the other ends of each of the members of each scissor assembly engaging the base and the frame, a screw and nut assembly, means securing the screw to one of the free ends of each of the scissor asemblies and preventing rotation of the screw, means for rotating the nut to cause movement axially of the ball screw to thereby cause movement of the free ends of each of the scissor assemblies to cause raising and lowering of the frame with respect to the base, a plurality of spaced apart shafts mounted on said frame and extending in an x direction, an x beam structure, bearing means carried by the shafts and supporting said x beam structure for movement in an x direction, power means connected between the frame and the x beam structure for causing movement of the x beam structure in an x direction, a y beam structure, means for supporting said y beam structure on said x beam structure for movement in a y direction, a patient couch mounted on the y beam structure, power means connected between the x beam structure and the y beam structure for causing movement of the patient couch in a y direction to cause the patient couch to be moved into and out of the opening in the magnet structure.

7. Apparatus as in claim 6 together with manually operated quick release means for coupling said patient couch to said y beam structure whereby in the event of a power failure with the patient couch in the opening, the patient couch can be readily removed from the opening.

8. In a three-axis patient positioning assembly for use with a magnetic resonance imaging apparatus of the type having a magnet structure with an opening therein, a base, a frame, at least first and second spaced apart scissor assemblies supporting said frame on said base for movement of said frame with respect to said base in a vertical or z direction, each of said scissor assemblies including first and second members which are pivotally innerconnected intermediate the ends of the same, means for fixing one end of one of the members of each scissor assembly to the base and one end of the other member to the frame, rollers carried by the other ends of each of the members of each scissor assembly engaging the base and the frame, a screw and nut assembly, means securing the screw to one of the free ends of each of the scissor assemblies and preventing rotation of the screw, means for rotating the nut to cause movement axially of the ball screw to thereby cause movement of the free ends of each of the scissor assemblies to cause raising and lowering of the frame with respect to the base, a plurality of spaced apart shafts mounted on said frame and extending in an x direction, an x beam structure, bearing means carried by the shafts and supporting said x beam structure for movement in an x direction, power means connected between the frame and the x beam structure for causing movement of the x beam structure in an x direction, a y beam structure, means for supporting said y beam structure on said x beam structure for movement in a y direction, a patient couch mounted on the y beam structure, power means connected between the x beam structure and the y beam structure for causing movement of the patient couch in a y direction to cause the patient couch to be moved into and out of the opening in the magnet structure and quick release means for coupling said patient couch to said y beam structure whereby in the event of a power failure with the patient couch in the opening, the patient couch can be readily removed from the opening, said y beam structure being provided with a slot , said means for coupling said patient couch to said y beam structure including a shaft extending longitudinally of the y beam structure, a linear actuator engaging the shaft and means coupling said quick disconnect means to said linear actuator.

9. Apparatus as in claim 8 wherein said y beam structure is provided with a slot extending longitudinally of the same and wherein said quick release mechanism extends through the slot.

10. Apparatus as in claim 9 together with flexible elongate sheet-like means covering said slot and movable vertically to travel over said quick release means as said patient couch is advanced and retracted on said y beam structure into and out of said opening, said flexible elongate sheet-like means being mounted in a fixed position longitudinally of the slot.

11. Apparatus as in claim 10 together with magnetic means for retaining said flexible sheet-like means over said slot.

12. In a magnetic imaging apparatus, a structure having an opening therein and adapted to receive an object to be imaged, an object platform sized so that it can be moved into and out of the opening of the magnetic structure, means for supporting said object platform, power actuator means for moving said object platform along a y axis into and out of the opening in said structure, said structure and said power actuator means including a slot underlying said object platform and means extending through said slot connecting said power actuator means to said object platform, flexible elongate sheet means covering said slot and traveling over the means connecting the object platform to the power actuator means as the object platform is moved into and out of the opening in the structure so that the portions of the slot not covered by the object platform are covered by the flexible elongate sheet means.

13. Apparatus as in claim 12 wherein said means connecting said object platform to said power actuator means includes quick release means for removing the object platform from within the opening in the structure in the event of a power failure.

* * * * *